(12) United States Patent
Cazalbou

(10) Patent No.: US 10,195,306 B2
(45) Date of Patent: *Feb. 5, 2019

(54) MODIFIED CERAMICS WITH IMPROVED BIOACTIVITY AND THEIR USE FOR BONE SUBSTITUTE

(71) Applicants: UNIVERSITE PAUL SABATIER TOULOUSE III, Toulous (FR); Centre national de la recherche scientifique, Paris (FR)

(72) Inventor: Sophie Cazalbou, Rebigue (FR)

(73) Assignees: UNIVERSITE PAUL SABATIER TOULOUSE III, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/380,227

(22) Filed: Dec. 15, 2016

(65) Prior Publication Data

US 2017/0165398 A1 Jun. 15, 2017

(30) Foreign Application Priority Data

Dec. 15, 2015 (EP) .................................... 15307012

(51) Int. Cl.
| | |
|---|---|
| *B01J 3/00* | (2006.01) |
| *A61L 27/32* | (2006.01) |
| *A61L 27/54* | (2006.01) |
| *C01B 25/32* | (2006.01) |
| *C04B 35/447* | (2006.01) |
| *C04B 41/50* | (2006.01) |
| *C04B 41/85* | (2006.01) |
| *A61L 27/12* | (2006.01) |
| *A61L 27/56* | (2006.01) |
| *C04B 41/00* | (2006.01) |

(52) U.S. Cl.
CPC ............. *A61L 27/32* (2013.01); *A61L 27/12* (2013.01); *A61L 27/54* (2013.01); *A61L 27/56* (2013.01); *B01J 3/008* (2013.01); *C01B 25/327* (2013.01); *C04B 35/447* (2013.01); *C04B 41/5072* (2013.01); *C04B 41/85* (2013.01); *A61L 2400/12* (2013.01); *A61L 2400/18* (2013.01); *A61L 2430/02* (2013.01); *A61L 2430/12* (2013.01); *A61L 2430/24* (2013.01); *C04B 41/009* (2013.01); *C04B 2235/447* (2013.01)

(58) Field of Classification Search
CPC .................................. B01J 3/008; A61L 27/32
See application file for complete search history.

(56) References Cited

U.S. PATENT DOCUMENTS

2010/0323094 A1 12/2010 Autefage et al.

OTHER PUBLICATIONS

European Search Report for EP 15307012, completed May 2, 2016.
Helene Autefage et al: "Adsorption and release of BMP-2 on nanocrystalline apatite-coated and uncoated hydroxyapatite/[beta]-tricalcium phosphate porous ceramics", Journal of Biomedical Materials Research. Part B: Applied Biomaterials, vol. 91B, No. 2, Nov. 1, 2009 (Nov. 1, 2009), pp. 706-715, XP055269475, US ISSN: 1552-4973, DOI: 10.1002/jbm.b.31447 * abstract * p. 707, col. 1, paragraph 5—p. 710, col. 2, paragraph 1.
Duarte A R C et al: "Processing of novel bioactive polymeric matrixes for tissue engineering using supercritical fluid technology", Materials Science and Engineering C, Elsevier Science S.A, CH, vol. 29, No. 7, Aug. 31, 2009(Aug. 31, 2009), pp. 2110-2115, XP026446080, ISSN: 0928-4931 [retrieved on Apr. 19, 2009] * abstract * p. 211, col. 2, paragraph 3.
Pamela Habibovic, et al: "Comparative in vivo study of six hydroxyapatite-based bone graft substitutes" Journal of Orthopaedic Research, vol. 26, Issue 10, Oct. 2008, pp. 1363-1370, Version of Record online : Apr. 10, 2008, DOI: 10.1002/jor.20648.

*Primary Examiner* — Gina C Justice
(74) *Attorney, Agent, or Firm* — B. Aaron Schulman, Esq.; Stites & Harbison, PLLC

(57) ABSTRACT

The present invention concerns ceramics having a modified surface with improved bioactivity, their process of preparation and their use for orthopedics, dentistry or reconstructive surgery, in particular for use as a bone filler.

6 Claims, 3 Drawing Sheets

MODIFIED CERAMICS WITH IMPROVED BIOACTIVITY AND THEIR USE FOR BONE SUBSTITUTE

Figure 1:
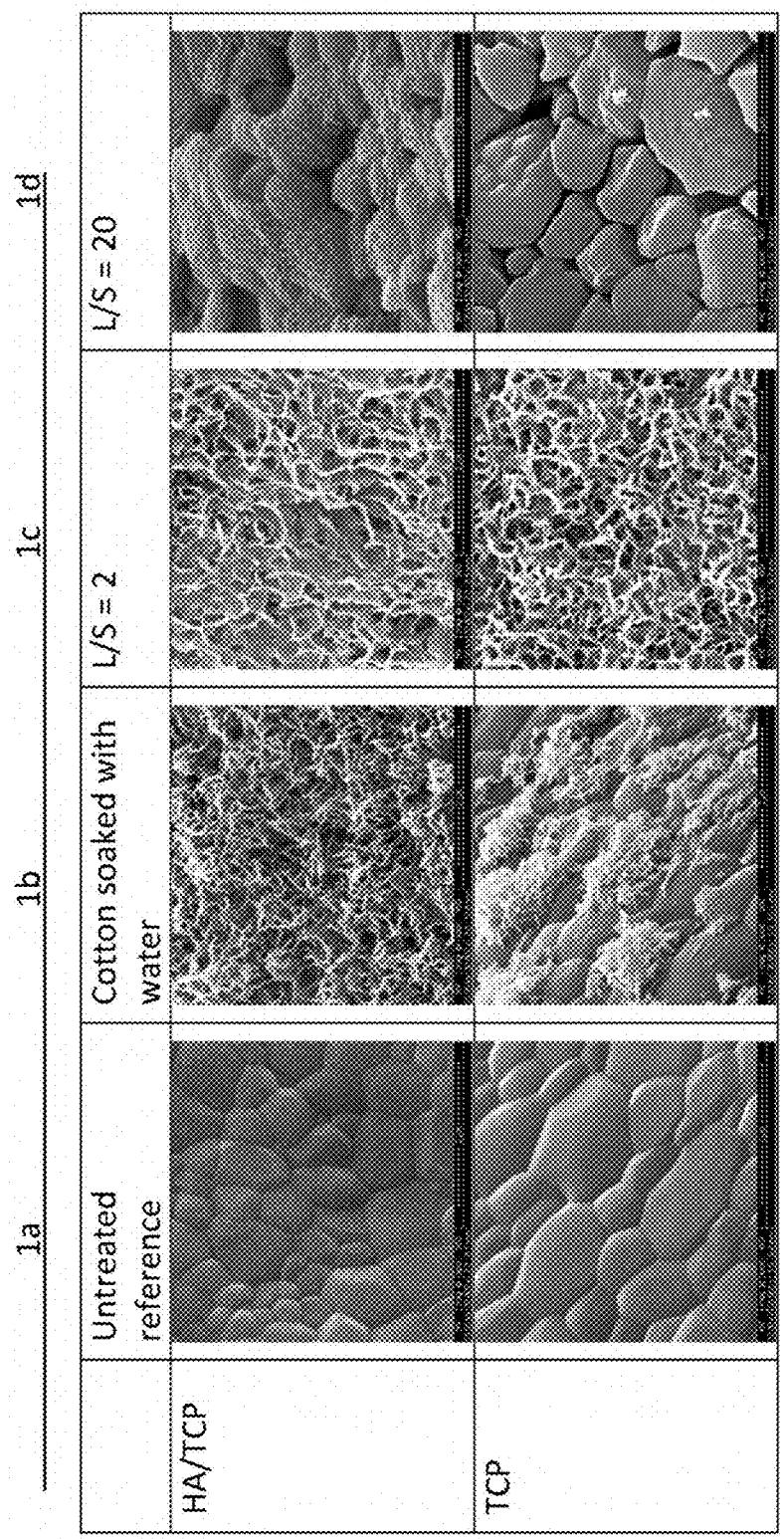

The present invention concerns the field of for orthopedics, dentistry or reconstructive surgery, and more particularly the field of bone filling materials.

The chemical composition of bone mineral is that of a carbonate containing apatite deficient in calcium ions and with a portion of the $PO_4$ groups substituted with $HPO_4$ and $CO_3$. Its chemical formula is $Ca_{8,3} \square_{1,7} (PO_4)_{4,3} (HPO_4)_{0,7} (CO_3)_{1,0} (CO_3,OH)_{0,3} \square_{1,7}$.

Its poorly crystallized apatite structure and the presence on the surface of crystals of labile environments make it very reactive, allowing it to participate in many exchange reactions with the surrounding ions in the body environment.

Calcium phosphates are the main constituents of hard tissues such as bones and teeth. It is the reason why over 40 years, research in bone filling materials has focused on the development of synthetic biomaterials obtained from various calcium phosphates.

Hydroxyapatite (HA) has thus become the reference compound in the field of bone substitutes as its composition is close to that of bone minerals and as it is stable at high temperature. This is why the first ceramics used as bone substitute were only composed with hydroxyapatite.

However, such bone substitutes are obtained at high temperature (>1000° C.) and are very poorly soluble in the body environment, so that residues may still usually be found in the bone implantation sites several years after implantation.

Lately, improved ceramics have made use of tricalcium phosphate (TCP) in order to improve the resorption. Used alone or most often associated with hydroxyapatite, TCP accelerates resorption of the material and increases the local release of calcium and phosphate, so as to promote new bone formation on the surface of hydroxyapatite.

The use of shaping processes associating blowing agents and adapted heat treatments have also helped to make considerable progress in improving the porosity of biomaterials used for bone filling.

The ceramics used today have a chemical composition close to that of bone minerals and an interconnected macroporous architecture similar to that of cancellous bone. These materials have significant benefits and are widely used when it comes to fill a bone defect. Nevertheless, they involve some disadvantages, including the followings:

Hydroxyapatite and tricalcium phosphate have the following chemical formula: $Ca_{10}(PO_4)_6(OH)_2$ and $Ca_3(PO_4)_2$, respectively. They thus have a chemical composition close but still different from those of bone minerals.

In addition, when subjected to elevated temperatures, these two stoechiometric compounds have a crystalline structure completely crystallized and hence unreactive.

In terms of morphology, the ceramics are typically constituted by particles welded together during sintering.

From a macroscopic point of view, materials having an important macroporous network are generally obtained; some heat treatments may sometimes lead to a microporous network. From a microscopic point of view, the absence of nano-sized or sub-micron porosity hinders the adsorption of proteins and limits their osteoconductive and/or osteoinductive properties.

Indeed, the presence of both micropores (with diameter lower than 10 μm) and nanopores plays an important role in the efficiency of reconstruction of these materials, particularly on their osteoconductive and/or osteoinductive properties [Habibovic et al., Journal of orthopaedic research, 2008, 1363-1370]. Due to their large size, the pores of the existing ceramics cannot welcome cells but can be used to their anchoring in the implant. It was also found that osteoblasts better adhered on nanoporous ceramics, whereas fibroblasts adhered less.

Autefage et al (J. Biomedical materials research, part B, 706-715, 2009) and US 2010/323094 disclose a ceramics, the surface of which is unmodified and merely covered by apatite crystals that are previously formed.

The objective of the invention is therefore to provide a macroporous calcium phosphate ceramic having a reactive surface that is nanoporous and having a chemical composition similar to that of bone minerals.

The present invention proposes to modify the surface of the calcium phosphate ceramics widely used in the field of orthopedics, dentistry or reconstructive surgery so as to obtain a material whose morphology is that of cancellous bone and the chemical composition of the surface is that of bone mineral itself.

Such modification has been found possible by submitting said ceramics to supercritical $CO_2$ in aqueous conditions.

According to a first object, the present invention thus provides a calcium phosphate ceramic having a modified surface, where said ceramic comprises:
hydroxyapatite (HA); or
tricalcium phosphate (TCP), or
a mixture thereof in the form of biphasic calcium phosphate (BCP),
characterized in that said ceramic comprises a nanoporous surface comprising deposited nanocrystals of apatite.

According to an embodiment, the nanocrsytals of apatite are precipitated and formed on the surface of the ceramics.

A "calcium phosphate ceramic" as used therein refers to any material comprising calcium and phosphate phases that may be used for biological applications, such as for bone repair, including bone filling or bone substitute. It is also called "bioceramic" hereafter.

The ceramics materials in accordance with the invention are primarily calcium phosphate ceramics generally obtained at high temperatures, that can be dense or porous. According to a particular embodiment, they are macroporous.

They are most often composed of hydroxyapatite (HA), tricalcium phosphate (TCP) or a mixture of these two compounds in the form of biphasic calcium phosphate (BCP) but may also contain phases such as fluorapatite (FHA) and/or chloro-apatite (CLHA).

According to an embodiment, the calcium phosphate ceramic according to the invention is such that it comprises calcium phosphate in anyone of the following forms:
Monocalcium phosphate monohydrate (MCPM) ($Ca(H_2PO_4)_2 \cdot H_2O$), Monocalcium phosphate anhydrous (MCPA) ($Ca(H_2PO_4)_2$), Dicalcium phosphate anhydrous (DCPA) ($CaHPO_4$), Dicalcium phosphate dihydrate (DCPD) ($CaHPO_4 \cdot 2H_2O$), Octacalcium phosphate (OCP) ($Ca_8H_2(PO_4)_6 \cdot 5H_2O$), α-Tricalcium phosphate (α-TCP) ($\alpha\text{-}Ca_3(PO_4)_2$), β-Tricalcium phosphate (β-TCP) ($\beta\text{-}Ca_3(PO_4)_2$), Amorphous calcium phosphate (ACP) ($Ca_3(PO_4)_2$), Hydroxyapatite (HA) ($Ca_{10}(PO_4)_6(OH)_2$), Tetracalcium phosphate (TTCP) ($Ca_4(PO_4)_2O$), as well as the deficient or ion-substituted calcium orthophosphates.

The ceramics according to the invention may be available in form of particulates, blocks, cements and coatings. They can be porous or dense and bioresorbable, or not. According to an embodiment, ceramics are bioceramics obtained by using high temperature (sintering, firing, plasma spray . . . ).

For example, porous calcium phosphate ceramics may be obtained by sponge replication, direct foaming techniques, vacuum-assisted foaming of a ceramic suspension (VFC), or freeze casting. Ceramics of the invention may also be calcium phosphate coating of porous material obtained by various methods such as plasma spray coating (but this process presents a very poor infiltration capacity of porous materials), by electrophoresis, by biomimetic approaches employing SBF solutions, saturated solutions or equivalent as well as other methods conducing to calcium phosphate coating of porous materials and/or macroporous calcium phosphate coating.

Such ceramics may be prepared according to the methodologies described in the literature, they may be commercially available, such as for example the ceramics sold under the following trade names:

MBC™ (Biomatlante, France), Ceraform™ (Teknimed, France), Interpore200™, Interpore, Netherlands), CrossBone™ (Biotech International, France), Bongros™ (CGBio, Korea), Bicalphos™ (Medtronic Sofamor Danek, USA), Syncera™ (Oscotec, Korea), BoneMedik™ (MetaBiomed Co, Korea), ACOR™ (Amplitude, France), Avantage Plasma HAP™ (Biomet, France), Secur Fit HA™ (stryker orthopaedics, USA).

The ceramic according to the invention may also be in the form of a coating on a metal.

"Modified ceramic" as used therein refers to a ceramic as defined above where its surface has been modified so as to include apatite nanocrystals.

Where the ceramic does not comprise the modified surface according to the invention, it is herein called "unmodified".

Said ceramic is unmodified when it is merely coated by crystals that are previously precipitated.

Said ceramic is modified when its surface is at least partly dissolved to form calcium and phosphate ions that are then reprecipitated in situ to form apatite nanocrystals that are deposited on the ceramics and grow over its surface.

"Surface" as used therein includes all surfaces of the ceramic which may be available to a fluid where said ceramic is immersed in such fluid. It includes both the outer surface delimiting the shape of the ceramic, as well as the inner surfaces, which in turn refer to the surfaces created by the pores of the ceramic, and are not necessarily visible from the outer shape of the ceramic.

"Modified surface" refers to the surface of a ceramic as modified above coated with nanocrystals of apatite.

"Nanocrystals" as used therein refers to crystals having a (size) average diameter of strictly less than 1 μm.

Said nanocrystals are deposited on the surface of the ceramic.

"Deposited" as used therein refers to the way such nanocrystals are precipitated and formed on the ceramics. Said crystals are generally precipitated on and grown over the surface of the ceramic so as to form a nanoporous coating on said surface.

"Deposited" as used herein therefore refers to nanocrystals that are formed in situ on the ceramics. It does not refer to the deposition of crystals that are formed beforehand.

The deposition according to the invention allows a fine layer to be formed.

The layer formed by the deposited nanocrystals has a thickness generally smaller than 10 μm.

"Macroporous" as used therein refers to the morphology of the ceramic comprising pores of (size) average diameter equal or greater than 1 μm.

"Nanoporous" as used therein refers to the morphology of the ceramic comprising pores of (size) average diameter strictly smaller than 1 μm.

The nanocrystals of the apatite present on the surface of the ceramic may be in particular nanocrystals of carbonated apatite, that are highly reactive towards the body environment.

From a morphological point of view, the modified ceramics of the invention having a modified surface have thus both an interconnected macroporosity that promotes cellular invasion and bone rehabilitation and a nanosized porosity which promotes protein adsorption and adhesion of osteoblasts responsible for bone formation.

The physicochemical and morphological properties of the modified ceramic of the invention may allow inter alliae:

A high reactivity and in particular a high capacity to react with the surrounding biological fluids, A greater superficial resorbability with capacity to release locally more ions essential for new bone formation, A greater adsorption capacity for different elements including proteins due to the presence of labile environments located on the surface of the crystal and due to the presence of nanosized porosity, An ability to promote cell adhesion and thus bone formation due to the nanosized porosity of the modified surface.

According to an embodiment, the modified surface of the ceramic of the invention may further comprise one or more additional bioactive components chosen from bioactive ionic species and active ingredients.

"Bioactive" as used therein refers to the capacity of the modified surface of the ceramic or the components thereof to interact with the biological environment where the modified ceramic of the invention is implanted.

Said bioactivity may involve exchanges such as ion exchanges between the components of the modified surface and those of the bodily fluids, and reactivity of the modified surface with the surrounding biological fluids or tissues.

Bioactive components of the modified surface of the invention include in particular ionic species such as $Mg^{2+}$, $Ag^+$, $Sr^{2+}$, $Zn^{2+}$, $Cu^{2+}$, $Ca^{2+}$, $Se^{2-}$, $Se^{4-}$. These elements are progressively released by the modified surface by ionic exchange with the ions contained in biological fluids or tissues, or during the resorption of the ceramic. Depending on the selected ion species, it is possible to promote bone formation by stimulating osteoblast activity (Mg, Sr) and/or reduce the risk of infection (Zn, Ag, Cu . . . ) and/or inflammation (Zn).

Bioactive components also include active substances such as drugs that may be incorporated within the modified surface.

The morphology of the modified surface may also be defined as bioactive, where the nanoporosity enhances the exchanges and the reactivity of the surface components with the surrounding biological fluids or tissues where there are implanted.

The modified ceramic of the invention may be useful for orthopedics, dentistry or reconstructive surgery.

According to a second object, the present invention provides for the use of the modified ceramic of the invention for orthopedics, dentistry or reconstructive surgery.

According to a third object, the present invention concerns a bone repair material comprising the modified ceramic according to the invention.

"Bone repair" as used therein refers to bone substitution or bone filling.

According to a fourth object, the present invention concerns a metal implant such as a prosthesis coated with a modified ceramic according to the present invention.

According to a fifth object, the present invention also concerns a process suitable for preparing modified ceramics according to the invention.

Accordingly, said process includes modifying the surface of a calcium phosphate ceramic comprising:
hydroxyapatite (HA); or
tricalcium phosphate (TCP), or
a mixture thereof (BCP).
where said process may comprise:
reacting said ceramic to supercritical $CO_2$ in the presence of an aqueous solution.

$CO_2$ in the supercritical state is commonly used in the field of organic biomaterial since it allows maintaining their three-dimensional structure during drying. However, it has never been used as the reactional medium of the mineral phases. According to the present invention, the $CO_2$ in the supercritical state unexpectedly allows to modify the chemical composition of the surface of the ceramics to obtain the same composition as that of bone mineral.

The aqueous solution may be water optionally comprising bioactive components such as drugs, ionic species (as Mg, Ag, Sr, Zn, Cu . . . ), or calcium or phosphate species, or can be simulated body fluid (SBF). SBF is a solution with an ion concentration close to that of human blood plasma.

The aqueous solution may also comprise one or more organic solvent miscible in $CO_2$, such as acetone, ethanol, methanol, chloroform, hexane, dimethylsulfoxide.

According to an embodiment, said aqueous solution may be water mixed with one or more organic solvent and is herein called "solution".

The ceramic may be immersed or in contact with a humid environment (e.g. a wet gauze) and placed in a reactor under supercritical $CO_2$ atmosphere.

According to an embodiment, phosphate ceramics are placed in an enclosed hydrated environment such as an aqueous medium reactor or in the presence of a small amount of said aqueous solution, for example a gauze impregnated with aqueous solution or ideally in a container which contains said aqueous solution.

Generally speaking, the amount of said solution optionally comprising one or more organic solvent should be sufficient to wet the whole surface of the ceramic but should not be too important as water may otherwise damage the ceramic during the processing by partial dissolution. The amount of the solution depends on the quantity and the nature of the ceramic. It can be determined by the skilled person by involving its skills and/or usual experiments.

According to an embodiment, the amount of the solution is such that the weight ratio of said solution (L) with respect to the ceramic (S) is comprised between 0.5 and 50.

Generally, the more dilute the solution, the smaller L/S.

Where the aqueous solution is water, the L/S ratio is generally comprised between 0.5 and 10, typically between 1 and 5.

In case of concentrated SBF solution, the L/S ratio may be comprised between 20 and 50.

According to an embodiment, the reaction may be carried out at a pressure comprised between 2 and 10 000 bar, generally not exceeding 200 bar, typically comprised between 60 and 150 bar.

According to an embodiment, the reaction may be carried out at a temperature comprised between 20 and 400° C., generally not exceeding 100° C., typically comprised between 30 and 50° C.

Typically, a supercritical $CO_2$ atmosphere may be achieved at temperature greater than 31° C. and pressure greater than 73.8 bar.

The modification of the surface of the ceramics is obtained by treating the material in the presence of water in a reactor under supercritical $CO_2$ atmosphere.

During the treatment in a supercritical $CO_2$ atmosphere, the water surrounding the material becomes saturated with $CO_2$. The pH of the solution decreases until reach a pH value around 4.

According to an embodiment, the reaction mixture may be maintained at an acid pH, generally lower than 6, typically around 4.

The acidic pH has the effect to induce a partial and superficial dissolution of the ceramic material. The partial dissolution of the ceramic surface leads to the release of phosphate ion and its counter ion, such as calcium ion and to a local pH rise.

During treatment, the $CO_2$ content in the atmosphere (in a gaseous or supercritical state) saturates the aqueous solution with dissolved carbonate ions thus decreasing its pH. The acidity of the aqueous solution caused by the dissolution of carbonate ions causes a superficial dissolution of the material.

Release of calcium and phosphate ions during superficial dissolution leads to a local sursaturation in calcium and phosphate ions, which causes the precipitation of biomimetic carbonated apatite nanocrystals. The apatitic structure of calcium phosphates being considered as very tolerant of ionic substitutions, during the precipitation, some ionic species present in the aqueous environment of the material integrates apatitic structure of nanocrystals. This is the way the carbonates and $HPO_4^{2-}$ ions come to substitute themselves for the ions $PO_4^{3-}$ and $OH^-$. When no additional active element is added, the environment consisting of calcium, phosphates ($HPO_4$ and $PO_4$) and carbonates ($CO_2$, $HCO_3$, $CO_3$), the precipitated crystals are carbonated apatite nanocrystals similar to bone minerals. This species will be released slowly related to the resorption of the ceramic. In addition, when additional active elements are introduced into the treatment solution, some of them integrate the labile environment as well as the crystalline structure of the new formed apatite nanocrystals while others react with dissolved carbonate ions and cause the precipitation of bioactive carbonate nanocrystals. The release of ionic species are then function to their rate of dissolution.

Moreover their organization on the surface of the material allows the creation of a porosity whose dimensions are significantly lower than that of the micron.

The resulting material has maintained its porous structure in a macroscopic scale but possesses from now a nanosized porosity (<1 µm) due to the precipitation of nanocrystals onto the surface of ceramic and present a surface composition similar to those of bone mineral.

The process of the invention is thus a straightforward—green—process, which uses $CO_2$ in the supercritical state and can be easily implemented on the industrial scale to achieve ceramics with an improved bioactivity.

According to an embodiment, bioactive components as defined above can be added during the process in order to provide a modified ceramic with a therapeutic activity from the material and/or allowing it to reduce post-operative complications (inflammation, infection).

Some drugs may also be added to the aqueous solution in dissolved state or in suspension in order to be bound to the nanocrystals during their formation and be released later in the body, once the ceramic is implanted.

Bioactive components such as ionic species (as Mg, Ag, Sr, Zn, Cu . . . ) can be added to the aqueous solution so as to introduce the apatitic structure of freshly precipitated nanocrystals.

Other ions such as calcium or phosphate may be added in order to promote the precipitation of the nanocrystals.

Accordingly, the aqueous solution used during the process may comprise the desired bioactive components.

FIGURES

Figure 2:
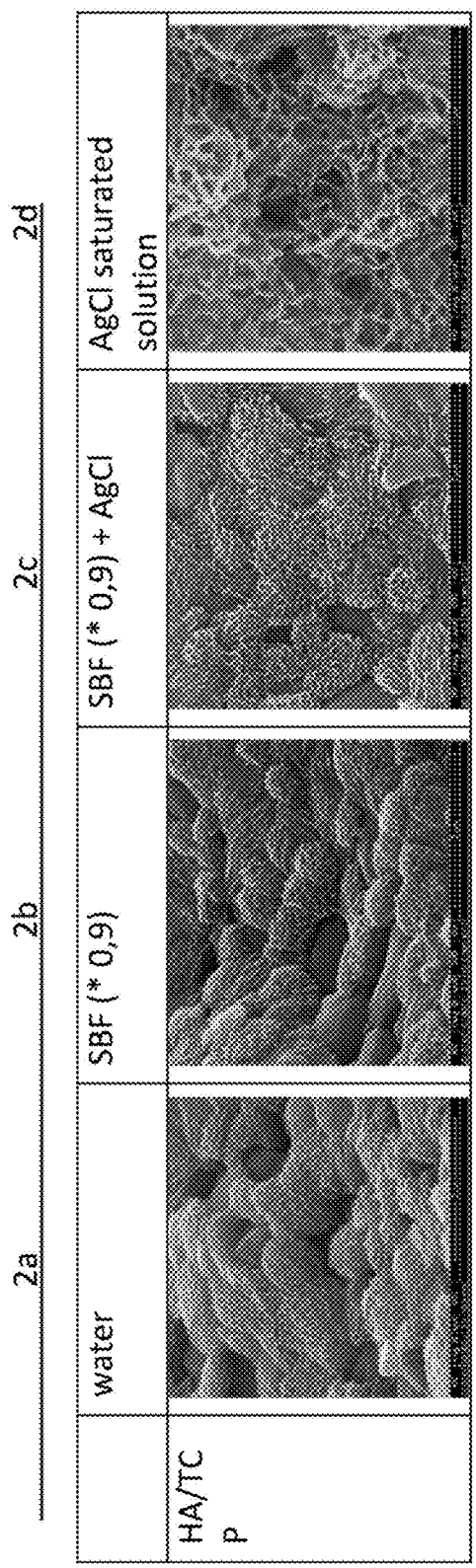

FIGS. 1 and 2 illustrate the influence of the quantity of the aqueous solution in the course of the process of preparation of the modified ceramics of the invention on the surface morphology. In FIG. 1, various L/S values are tested where the aqueous solution is water. In FIG. 2, L/S is 20 and both water and SBF solution are tested as aqueous solutions.

Figure 3:
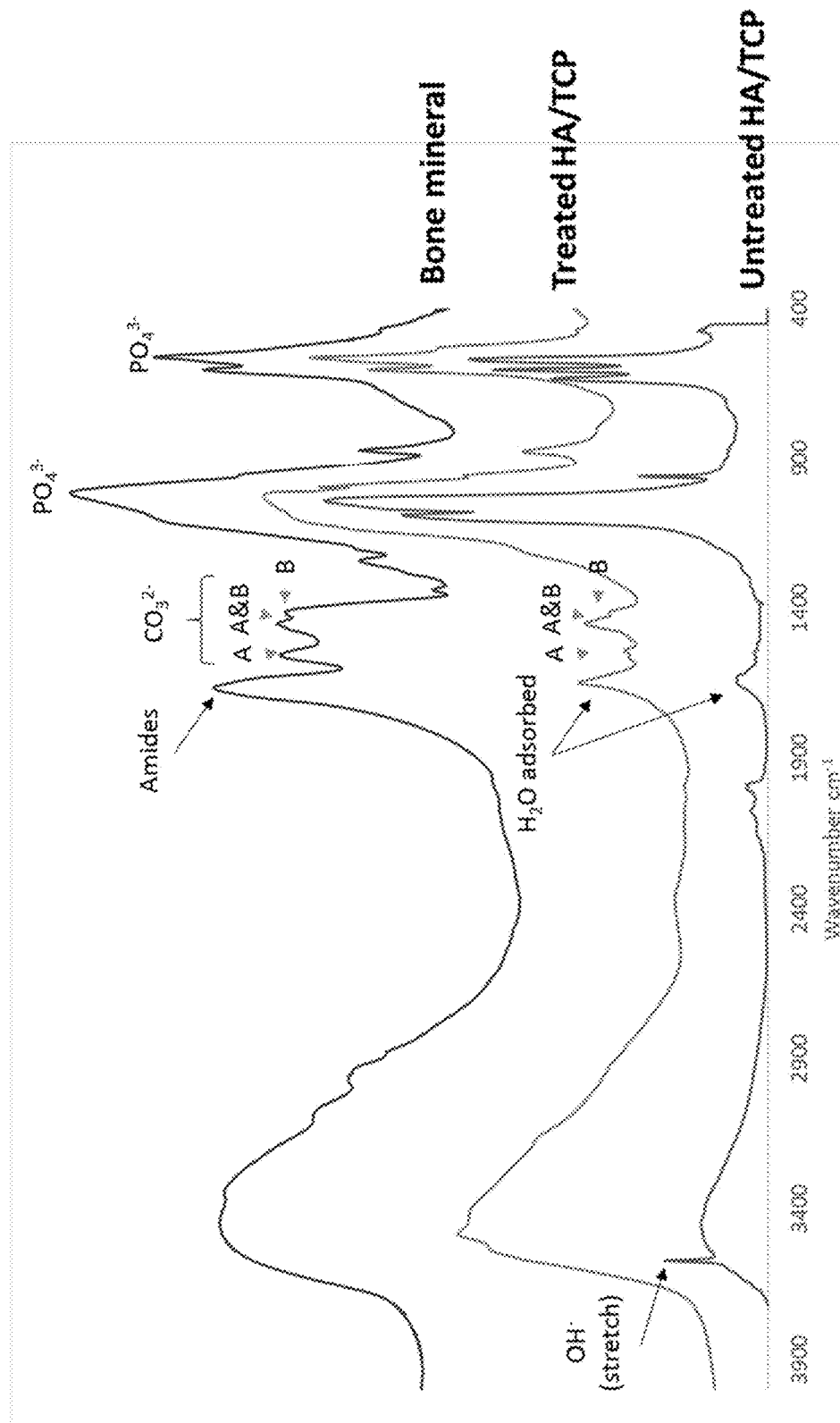

FIG. 3 illustrates the FTIR spectra of an unmodified ceramic and of a modified ceramic with comparison to bone mineral.

The following examples are given as a non-limiting illustration of the various objects of the invention.

EXAMPLE 1

Teatment of HA/TCP Ceramics Confined in Wet Cotton during 30 h at 50° C. and 100 Bar Ceramic cubes with dimension 3 mm*3 mm*3 mm (1.45 g) consist in 65% hydroxyapatite (HA) and 35% tricalcium phosphate (TCP). Their total porosity is between 60 and 85% and the pore size is between 150 and 400 µm. The cubes are evenly distributed between two hydrophilic cottons.

The assembly is then placed in a container with 9.96 g water and then placed under vacuum so as to favor the penetration of water inside the porous ceramic network. The L/S ratio is 6.88. The vacuum is then cut and the whole (cotton+ceramics) slightly wrung to remove excess water. The assembly is then placed in the chamber of a supercritical $CO_2$ dryer. The chamber temperature is raised to a temperature of 5° C. and then the chamber is filled in ⅔ full with liquid $CO_2$. The temperature of the chamber is gradually increased to 50° C. and the pressure adjusted to 100 bar.

After 30 hours of treatment, the pressure is reduced to atmospheric pressure and the assembly is removed from the enclosure. Ceramic cubes were then dried in the cotton in an oven at 50° C. for 48 h.

The morphology of the surface of the material is assessed by scanning electron microscopy and compared to the initial surface of the same material before treatment. The surface of the treated material has a large amount of entangled nanocrystals, characteristics of poorly crystallized apatite crystals. Tangling induces the formation of a nanoscale porosity.

EXAMPLE 2

Treatment of HA/TCP Ceramics Confined in Wet Cotton during 7 Days at 50° C. and 100 Bar Ceramics and protocol used are identical to those described in Example 1. However, the processing time is 7 days. The morphology of the surface of the material is assessed by scanning electron microscopy (FIG. 1b) and compared to the initial surface of the material (FIG. 1a). The surface of the treated material has a large amount of entangled nanocrystals characteristics of poorly crystallized apatite crystals. The difference of crystal morphology compared to those observed in Example 1 is due to the fact that, during treatment, over time, the apatitic nanocrystals mature and their crystallinity is improved. Indeed, poorly crystallized apatite are very reactive phases that evolve over time, in the presence of water. This maturation of apatitic phases has the effect of improving the crystallinity and decreasing their reactivity.

EXAMPLE 3

Treatment of HA/TCP Ceramics Confined in Container with small amount of Water (L/S=2) during 30 h at 50° C. and 100 Bar Ceramic cubes with dimension 3 mm*3 mm*3 mm (0.66 g) consist in 65% hydroxyapatite (HA) and 35% tricalcium phosphate (TCP). Their total porosity is between 60 and 85% and the pore size is between 150 and 400 µm. Cubes are placed in a container with just enough water to cover all the cubes (1.33 g) so that L/S=2.02. The whole is dipped into liquid nitrogen to freeze the water. Once the cubes in the ice, the container is placed in the chamber of a supercritical $CO_2$ dryer.

The chamber temperature is raised to a temperature of 5° C. and then filled in ⅔ full with liquid $CO_2$. The temperature of the chamber is gradually increased to 50° C. and the pressure adjusted to 100 bars.

After 30 hours of treatment, the pressure is reduced very gradually to atmospheric pressure and the assembly is removed from the enclosure. Ceramic cubes were then dried in an oven at 50° C. for 48 h.

The morphology of the surface of the material is assessed by scanning electron microscopy and compared to the initial surface of the material. The surface of the treated materials has a large amount of entangled nanocrystals characteristics of poorly crystallized apatite crystals. The arrangement of some crystals creates on the surface of the material porous spheres of a size not exceeding 3 µm.

EXAMPLE 4

Treatment of TCP Ceramics Confined in Container with small amount of Water (L/S=2) During 30 h at 50° C. and 100 Bar Ceramic cubes with dimension 3 mm*3 mm*3 mm (0.86 g) consist in 100% tricalcium phosphate (TCP). Their total porosity is between 60 and 85% and the pore size is between 150 and 400 µm. The protocol used is identical to those described in example 3, with 1.76 g of water (L/S=2.05).

The morphology of the surface of the material is assessed by scanning electron microscopy (FIG. 1c) and compared to the initial surface of the material (FIG. 1a).

The surface of the treated materials has a large amount of entangled nanocrystals characteristics of poorly crystallized apatite crystals.

EXAMPLE 5

Treatment of HA/TCP Ceramics confined in Container with Large amount of Water (L/S=20) during 30 h at 50° C. and 100 Bar Ceramic cubes with dimension 3 mm3 mm*3 mm (0.72 g) consist in 65% hydroxyapatite (HA) and 35% tricalcium phosphate (TCP). Their total porosity is between 60 and 85% and the pore size is between 150 and 400 μm.

The cubes are placed into a container with 14.44 g of water (L/S=20.05). The treatment performed is identical to that described in Example 3.

The morphology of the surface of the material is assessed by scanning electron microscopy and compared to the initial surface of the material (FIG. 1a). The surface of the treated materials brings up an important modification of the morphology of the ceramic skeleton with dissolution of TCP grains. Nevertheless, some nanocrystals precipitated on the surface of the ceramic. The coated surface corresponds to the surface which was at the bottom of the container, that is to say in a space where the diffusion of the dissolved species is more limited. The observations allow us to say that the treatment of the ceramic must be done in a confined aqueous environment with an amount of water that allows full wetting of the ceramic but prevents diffusion and dispersion of dissolved ionic species.

EXAMPLE 6

Treatment of TCP Ceramics confined in Container with Large amount of Water (L/S=20) during 30 h at 50° C. and 100 Bar Ceramic cubes with dimension 3 mm*3 mm*3 mm (0.856 g) consist in 100% tricalcium phosphate (TCP). Their total porosity is between 60 and 85% and the pore size is between 150 and 400 μm.

The cubes are placed into a container with 17.21 g of water (L/S=20.1). The treatment performed is identical to that described in Example 3.

The morphology of the surface of the material is assessed by scanning electron microscopy (FIG. 1d) and compared to the initial surface of the material (FIG. 1a).

The surface of the treated materials brings up an important modification of the morphology of the ceramic skeleton with dissolution of TCP grains.

The resulting material is friable. As indicated in Example 5, the observations allow us to say that the treatment of the ceramics has to be made in a confined aqueous environment with an amount of water which enables total wetting of the ceramic but prevents diffusion and dispersion of the dissolved ionic species.

EXAMPLE 7

Treatment of HA/TCP Ceramics confined in Wet Cotton during 24 h at 20° C. and 60 Bar in Liquid $CO_2$ Cubes treated are the same than those used in example 1.

They are, as indicated in example 1, ceramic cubes with dimension 3 mm*3 mm*3 mm (0.9757 g), placed between two wet cotton wool discs then wringed. The amount of water was 9.66 g. The L/S ratio is 9.9 g.

Contrary to example 1, the temperature used to realize the treatment is 20° C. with a pressure of 60 bars. In these conditions, the whole is maintained for 24 hours in the $CO_2$ in the liquid state.

After 24 hours of treatment, the pressure is reduced to atmospheric pressure and the assembly is removed from the enclosure. Ceramic cubes are then dried in the cotton in an oven at 50° C. for 48 h.

The morphology of the surface of the material is assessed by scanning electron microscopy and compared to the initial surface of the material. The surface of the treated material presents formation of apatite nanocrystals but a partial dissolution of the particles that constitute the ceramic is observed. As in Example 4, the ions released during treatment are broadcast then dispersed in the solution preventing the local supersaturation and the precipitation of the nanocrystals.

This example allows us to affirm that whatever the fluid, the amount should not allow significant diffusion of calcium and phosphate ions and prevent the establishment of a local supersaturation failing to prevent the precipitation of apatite nanocrystals.

EXAMPLE 8

Treatment of TCP Ceramics confined in Wet Cotton during 24 h at 20° C. and 60 Bar in Liquid $CO_2$ The cubes are similar to those used in example 4 and treatment is similar to those used in example 7, with 1.64 g of ceramic and 9.96 g of water (L/S=6.07).

The morphology of the surface of the material is assessed by scanning electron microscopy and compared to the initial surface of the material (FIG. 1a).

The observations are identical to those made in Example 7. The surface of the treated material has nanocrystals of apatite but a partial dissolution of the particles constituting the ceramic is observed.

EXAMPLE 9

Treatment of Non-calcined Hydroxyapatite Powders

The uncalcined hydroxyapatite powders (4.89 g of powder in cotton impregnated with 7.29 g of water, L/S=1.49) are treated according to the protocol described in example 1, but treatment times and temperatures are different (30 h, 50° C. and 100 bar). The Fourier transformation infrared spectroscopy spectra are shown in FIG. 3 and compared with the spectrum of untreated powder (FIG. 3).

In FIG. 3, the FTIR spectra highlight chemical modifications of the powder with substitution of a part of $PO_4^{3-}$ groupments with $CO_3^{2-}$ (type B $CO_3$) and $HPO_4^{2-}$ ions as well as $OH^-$ ions by $CO_3^{2-}$ (type A $CO_3$).

The FTIR spectra of the treated powder showed that the moist environment promotes the conversion of hydroxyapatite in carbonated apatite. Furthermore, they allow to identify the substitution of a portion of the $PO_4$ by $HPO_4$ and $CO_3$ ions and a portion of the OH ions by $CO_3$.

The chemical composition of the powders obtained is similar to that of bone mineral. The chemical composition and crystallinity apatite crystals can be adjusted by the parameters used during the treatment until obtain the same composition of bone mineral more or less matured. Indeed, over time, the bone mineral consists of nanocrystals having a crystallinity increases and the amount of $CO_3$ ions increases with a decrease in $HPO_4$ ions.

EXAMPLE 10

Treatment of HA/TCP Ceramics confined in Container with Small amount of Aqueous Solution containing Bioactive Ionic Species during 10 h at 50° C. and 100 Bar Ceramic cubes with dimension 3 mm*3 mm*3 mm (0.82 g) consist in 65% hydroxyapatite (HA) and 35% tricalcium phosphate (TCP). Their total porosity is between 60 and 85% and the pore size is between 150 and 400 μm. The treatment is similar to those used in example 3 but carried out during 10 h.

Moreover, in this example, the water is replaced with 2.23 g of a solution containing 25 mM $Ca^{2+}$, 2 mM $Mg^{2+}$, 2 mM $Sr^{2+}$ and 10 mM $HPO_4^{2-}$. L/S=2.8.

During treatment, all the ionic species present in the ceramic environment contribute to the formation of apatite nanocrystals. The crystals thus formed are poorly crystallized apatite in which part of Ca ions are substituted by magnesium (Mg) and strontium (Sr) ions (known for their ability to stimulate osteoblast activity). The addition into solution of $Ca^{2+}$ and $HPO_4^{2-}$ ions reduces the treatment time and reduce the dissolution of the ceramic surface. In fact, the saturation in ionic species at the surface of the ceramic is reached quickly and is not related to the calcium and phosphate ions released during the treatment that is to say superficial by the ceramic.

EXAMPLE 11

Treatment of HA/TCP Ceramics confined in Container with Large amount of Aqueous Diluted SBF Solution (L/S=20) during 30 h at 50° C. and 100 Bar Ceramics and protocol used are identical to those described in Example 5. However, the solution used during treatment consists in diluted SBF solution (SBF*0.9). The amount of solution used correspond to L/S=20. The treatment in supercritical $CO_2$ atmosphere is realized during 30 h at 50° C. and 100 bar.

The morphology of the surface of the material is assessed by scanning electron microscopy (FIG. 2b) and compared to the surface of the same material treated in the same condition with water (FIG. 2a).

EXAMPLE 12

Treatment of HA/TCP Ceramics confined in Container with Large amount of Aqueous Diluted SBF Solution containing Bioactive Ionic Species (L/S=20) during 30 h at 50° C. and 100 Bar Ceramics and protocol used are identical to those described in Example 11. However, the solution used during treatment consists in diluted SBF solution (SBF*0.9) in which AgCl salt is introduced until saturation.

The amount of solution used correspond to L/S=20. The treatment in supercritical $CO_2$ atmosphere is realized during 30 h at 50° C. and 100 bar.

The morphology of the surface of the material is assessed by scanning electron microscopy (FIG. 2c) and compared to the surface of the same material treated in the same condition with water (FIG. 2a).

EXAMPLE 13

Treatment of HA/TCP Ceramics confined in Container with Large amount of Aqueous Solution containing Bioactive Ionic Species (L/S=20) during 30 h at 50° C. and 100 Bar Ceramics and protocol used are identical to those described in Example 11. However, the solution used during treatment consists in AgCl saturated solution.

The amount of solution used correspond to L/S=20. The treatment in supercritical CO2 atmosphere is realized during 30 h at 50° C. and 100 bar.

The morphology of the surface of the material is assessed by scanning electron microscopy (FIG. 2d) and compared to the surface of the same material treated in the same condition with water (FIG. 2a).

FIG. 2 shows that when the amount of solution used is very important (ex: L/S=20), the use of SBF solution, even diluted, ie not having reached the metastable state (ex: SBF*0.9) reduces the damage of the ceramic. The use of bioactive ions (ex: $Ag^+$) can be envisaged, introduced into the SBF solution or in water. Their use does not prevent the surface modifications of the ceramic and allows firstly the precipitation on the surface of the ceramic of $Ag^+$ substituted apatitic nanocrystals and secondly, the precipitation of silver carbonate nanocrystals. The therapeutic activity of the ceramic will be due to the choice of the ions used and to their staged release related to the dissolution rate of active nanocrystals: fast for carbonate crystals and slower for apatitic crystals.

The invention claimed is:

1. A process for modifying a macroporous calcium phosphate ceramic comprising:
hydroxyapatite (HA), or
tricalcium phosphate (TCP), or
a mixture thereof in the form of biphasic calcium phosphate (BCP), said process comprising:
reacting said ceramic with supercritical $CO_2$ in the presence of an aqueous solution.

2. The process according to claim 1 wherein the aqueous solution comprises one or more organic solvents.

3. The process according to claim 1, wherein the quantity of the solution is such that the weight solution/ceramic ratio (L/S ratio) is comprised between 0.5 and 50.

4. The process according to claim 1, wherein the reaction is carried out at a pressure comprised between 2 and 10000 bar and a temperature comprised between 20 and 400° C.

5. The process according to claim 1, wherein the reaction is carried out at a pressure comprised between 60 and 150 bar and a temperature comprised between 30 and 50° C.

6. The process according to claim 1 wherein the reaction mixture is maintained at an acid pH.

* * * * *